United States Patent
Sembritzki

(12) 
(10) Patent No.: US 6,792,067 B2
(45) Date of Patent: Sep. 14, 2004

(54) METHOD OF CORRECTING THE EXTRAFOCAL RADIATION OF AN X-RAY TUBE IN COMPUTED TOMOGRAPHY

(75) Inventor: Otto Sembritzki, Wachenroth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/442,135

(22) Filed: May 21, 2003

(65) Prior Publication Data

US 2004/0005036 A1 Jan. 8, 2004

(30) Foreign Application Priority Data

May 22, 2002 (DE) .......................................... 102 22 702

(51) Int. Cl.[7] .................................................. A61B 6/03
(52) U.S. Cl. .................................. 378/4; 378/7; 378/15; 378/901
(58) Field of Search .............................. 378/4, 7, 8, 15, 378/19, 901

(56) References Cited

U.S. PATENT DOCUMENTS 6,366,638 B1    4/2002   Hsieh et al.

2003/0058994 A1 * 3/2003  Sembritzki .................. 378/108

FOREIGN PATENT DOCUMENTS

DE          10123816        11/2001

\* cited by examiner

*Primary Examiner*—David V Bruce
(74) *Attorney, Agent, or Firm*—Harness, Dickey & Pierce, P.L.C.

(57) ABSTRACT

A method of correcting the extrafocal radiation of an X-ray tube in image recordings with a computed tomograph, includes subjecting measured data, obtained from detector channels of at least one detector row in the computed tomography, to logarithmic manipulation and back projection in order to obtain the image recordings. The measured data, before the logarithmic manipulation and back projection, is subjected to convolution with a detector-channel-dependent convolution core $EN(k)$, which is derived from a distribution of the extrafocal radiation on at least one detector channel of the computed tomograph or a computed tomograph of an identical type. The present method permits good correction of the extrafocal radiation without reference to the convolution cores to be used for the filtered back projection.

20 Claims, 4 Drawing Sheets

METHOD OF CORRECTING THE EXTRAFOCAL RADIATION OF AN X-RAY TUBE IN COMPUTED TOMOGRAPHY

The present application hereby claims priority under 35 U.S.C. §119 on German patent application number DE 10222702.0 filed May 22, 2002, the entire contents of which are hereby incorporated herein by reference.

FIELD OF THE INVENTION

The present invention generally relates to a method of correcting the extrafocal radiation of an X-ray tube in image recordings with a computed tomograph, preferably with which measured data obtained from detector channels of at least one detector row in the computed tomograph are subjected to logarithmic manipulation in order to obtain the image recordings.

BACKGROUND OF THE INVENTION

A computed tomograph includes, inter alia, an X-ray tube, at least one detector row with individual X-ray detectors, also referred to as detector channels below, and a patient support table. The X-ray tube and X-ray detectors are arranged on a gantry which, during the measurement, rotates about the patient support table or an examination axis running parallel to the latter. Alternatively to this, the X-ray detectors can also be arranged on a stationary detector ring around the patient support table, only the X-ray tube moving with the gantry.

As a rule, the patient support table can be displaced along the examination axis relative to the gantry. The X-ray tube produces a beam widened in a fan shape in a layer plane at right angles to the examination axis. The boundary of this beam in the direction of the layer thickness is set by the size or the diameter of the focus on the target material of the X-ray tube and one or more aperture stops arranged in the beam path of the X-ray beam. In addition, the angle of the fan-like widening of the beam is defined by an aperture stop arranged in front of the X-ray tube. During image recordings with the computed tomograph, the X-ray beam passes in the layer plane through a layer of an object, e.g. a layer of the body of a patient, which is mounted on the patient support table, and strikes the X-ray detectors of the detector row lying opposite the X-ray tube. The angle at which the X-ray beam penetrates the layer of the body of the patient and, if appropriate, the position of the patient support table relative to the gantry change continuously during the image recording with the computed tomograph.

During the measurement with a computed tomograph, a number of sets of measured data are obtained, which correspond to different projections of the respective transilluminated layer. A set of projections which have been recorded at various positions of the gantry during the rotation of the gantry around the patient is designated a scan. The computed tomograph records many projections at different positions of the X-ray source relative to the body of the patient, in order to reconstruct an image which corresponds to a two-dimensional slice (sectional image) of the body of the patient. For this purpose, following its logarithmic manipulation, the measured data is initially convoluted with a convolution core which, taking into account the physical relationships and the measuring system, produces specific image characteristics and then transforms them into the Cartesian space of the image in order to reconstruct the two-dimensional slice. This technique is also designated filtered back projection. The convolution cores used in the convolution are set up in accordance with the desired image characteristics or are known for a large number of such image characteristics. These image characteristics can be, for example, high local resolution or good low-contrast detectability. Using a suitable convolution core, the desired image characteristic in the reconstructed slice can be achieved.

During image recordings with computed tomographs, however, image artifacts can occur, which can be attributed to the undesired extrafocal radiation produced by the X-ray tube. The extrafocal radiation is produced outside the focal spot of the X-ray tube by backscattered electrons which fall back onto the anode of the X-ray tube. During the generation of this extrafocal radiation in the environment of the focal spot or focus of the X-ray tube, this cannot be masked out by the aperture stop on the tube side for bounding the fan-like beam, and is concomitantly registered by the detector channels of the detector row. This extrafocal radiation, which depends on the X-ray tube used, leads for example to what is known as the cupping effect in cranial tomograms of adults or to what is known as the halo effect in cranial tomograms of children.

In order to suppress the undesired image artifacts caused by extrafocal radiation, hitherto the convolution cores used for the filtered back projection have been manipulated in a suitable way in order to obtain an improved image quality. The convolution cores differ, however, depending on the object or object region respectively examined. For example, depending on the region of the body examined (head or body) and the age of the patient (adult or child), they must be different. Furthermore, these convolution cores must be matched to each computed tomograph and, in addition, do not supply optimal image results with regard to the suppression of the extrafocal radiation.

SUMMARY OF THE INVENTION

An object of an embodiment of the present invention is to specify a method of correcting the extrafocal radiation of an X-ray tube in image recordings with a computed tomograph which supplies good image results and requires no distinction between individual convolution cores.

In the method of an embodiment of the application of correcting the extrafocal radiation of an X-ray tube during image recordings with a computed tomograph, the measured data obtained from the detector channels of at least one detector row of the computed tomograph are subjected to logarithmic manipulation and, if appropriate, filtered back projection, in order to obtain the image recordings of the object examined. In the method of an embodiment of the application, the measured data from each detector channel, before the logarithmic manipulation and back projection, is subjected to convolution with a detector-channel-dependent convolution core, which is derived from a distribution of the extrafocal radiation on at least one detector channel of the computed tomograph or a computed tomograph of the same type. This distribution of the extrafocal radiation on the detector channel can in this case be obtained from a measurement with the detector channels or else by other ways, for example via the blackening of an X-ray film.

By way of this convolution of the measured data before the logarithmic manipulation, with the aid of a previously determined convolution function, virtually complete correction of the extrafocal radiation is possible. In particular, this correction does not require any distinction between the convolution cores for different regions of the body and ages of the patients. Instead, following the logarithmic manipulation, the correction supplies logarithmically manipulated raw data which no longer has to be subjected to any further physical correction of the extrafocal radiation. The subsequent back projection or reconstruction is carried out with this corrected raw data and can be carried out with any desired known convolution cores without a correction component for the extrafocal radiation.

The method of an embodiment of the application is based on the finding that the extrafocal radiation produces detector-channel-specific errors and can be described by a convolution process. As a result, correction by way of convolution of measured data is approximately possible, as carried out by the method of an embodiment of the application. A precondition for the derivation of the convolution core is the determination of the distribution of the extrafocal radiation for each individual detector channel or region of detector channels. The intensity of the extrafocal radiation can be determined or measured for a combination of tube and CT device type and then supplies the correction and the convolution cores for all devices of this type combination.

To derive the convolution core for a detector channel, the impulse response of the extrafocal radiation of the computed tomograph is preferably determined first and Fourier transformed. The Fourier transform is then inverted and transformed back again, in order in this way to obtain the convolution core for this detector channel. By way of such a simple inversion of the impulse response in Fourier space, a convolution core is obtained which already leads to very good image results, that is to say to very good suppression of the image artifacts caused by the extrafocal radiation. The impulse response can be determined, for example, by introducing an element that absorbs X-rays and has an edge into the X-ray beam, measuring the X-rays arriving at the detector channels of the detector row and subsequent differentiation of the step response. The absorbing element can, for example, be a lead plate, which is arranged at a distance from the detector elements of the detector row, between the X-ray tube and the detector row. The edge of the absorbing element is in this case positioned in such a way that the focus of the X-ray tube is covered for some of the detector channels or detector elements. Using this arrangement, the impulse response and thus the convolution core is determined for that detector channel on whose connecting line to the focus of the X-ray tube the edge of the absorbing element is located.

In place of the element with the edge, an aperture stop with a slit which is narrow as compared with the width of the focus of the X-ray tube can also be used. Using this slit aperture stop, the impulse response of the extrafocal radiation is measured directly, so that the differentiation step is dispensed with.

The impulse responses and convolution cores for the remaining detector channels can be obtained either by means of an appropriate measurement, that is to say by displacing the absorbing element, or calculated from the impulse response of the first measured detector element and the geometric data of the computed tomograph. In this calculation, use is made of the fact that the anode window of the X-ray tube, which is visible from the individual detector elements and predefined by the opening of the aperture stop on the tube side, and the associated distribution of the extrafocal radiation on the respective detector channels, as a function of the position of the detector channel within the detector row, to a good approximation change only on the basis of the geometric conditions. The distribution of the extrafocal radiation on the respective detector element in this case corresponds to a projection of the anode window onto the detector in each case. While, during the projection through the rotational centre of the computed tomograph, the anode window is projected symmetrically onto the central detector region, the projection of the anode window outside the rotational centre of the computed tomograph takes place unsymmetrically and with a different length. However, this is a purely geometrical effect, which can therefore be calculated easily.

In the preferred embodiment, the convolution core is determined for one of the central detector channels by the edge of the absorbing element being positioned at the rotational centre of the computed tomograph during the measurement of the impulse response.

When carrying out the method of an embodiment of the application, it is not necessary for a separate convolution core to be provided for each individual detector channel. The detector row can instead be divided into a number of regions of detector channels following one another, in each case the same convolution core being used for the detector channels of a region. In this embodiment, the correction of the extrafocal radiation is carried out in a region-dependent manner. By using the same convolution core for a specific number of adjacent detector channels, the number of convolution cores is reduced, and therefore does not have to be equal to the number of detector channels.

BRIEF DESCRIPTION OF THE DRAWINGS

The present invention will be explained briefly again below using an exemplary embodiment in conjunction with the drawings, without restricting the general idea of the invention. In the drawings.

DETAILED DESCRIPTION OF THE PREFERRED EMBODIMENTS

Figure 1:
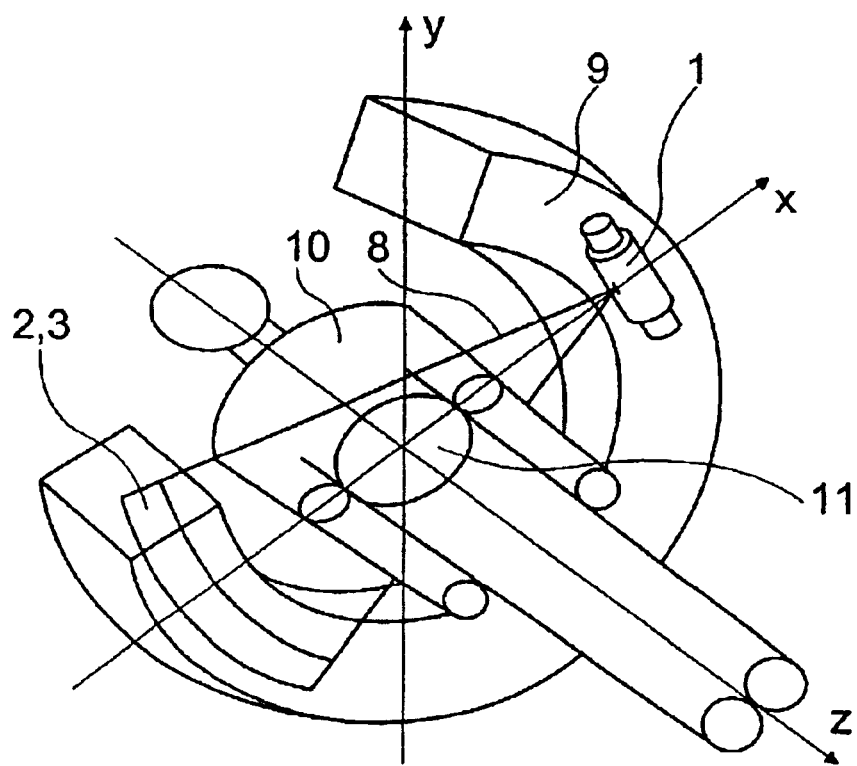
FIG. 1 shows a schematic view of part of a computed tomograph for obtaining slices from a layer of the body of a patient.

FIG. 1 shows a schematic view of part of a computed tomograph to illustrate the geometrical relationships in the image recording. The computed tomograph has an X-ray source in the form of an X-ray tube 1, which emits a fan-like X-ray beam 8 in the direction of a detector row 2 of a relatively large number of successive detectors or detector channels 3. Both the X-ray tube 1 and the detector row 2 are arranged on a gantry 9, which can rotate continuously about a patient 10. The patient 10 lies on a patient support table, not illustrated in FIG. 1, which extends into the gantry 9. The gantry 9 rotates in an x-y plane in a Cartesian coordinate system x-y-z indicated in FIG. 1. The patient support table can be moved along the z axis, which corresponds to the layer thickness direction of the layers of the patient 10 to be represented in each case. In the figure, it is also possible to see the layer 11 which is transilluminated by the X-ray beam 8 and of which a slice is to be produced.

Figure 2:
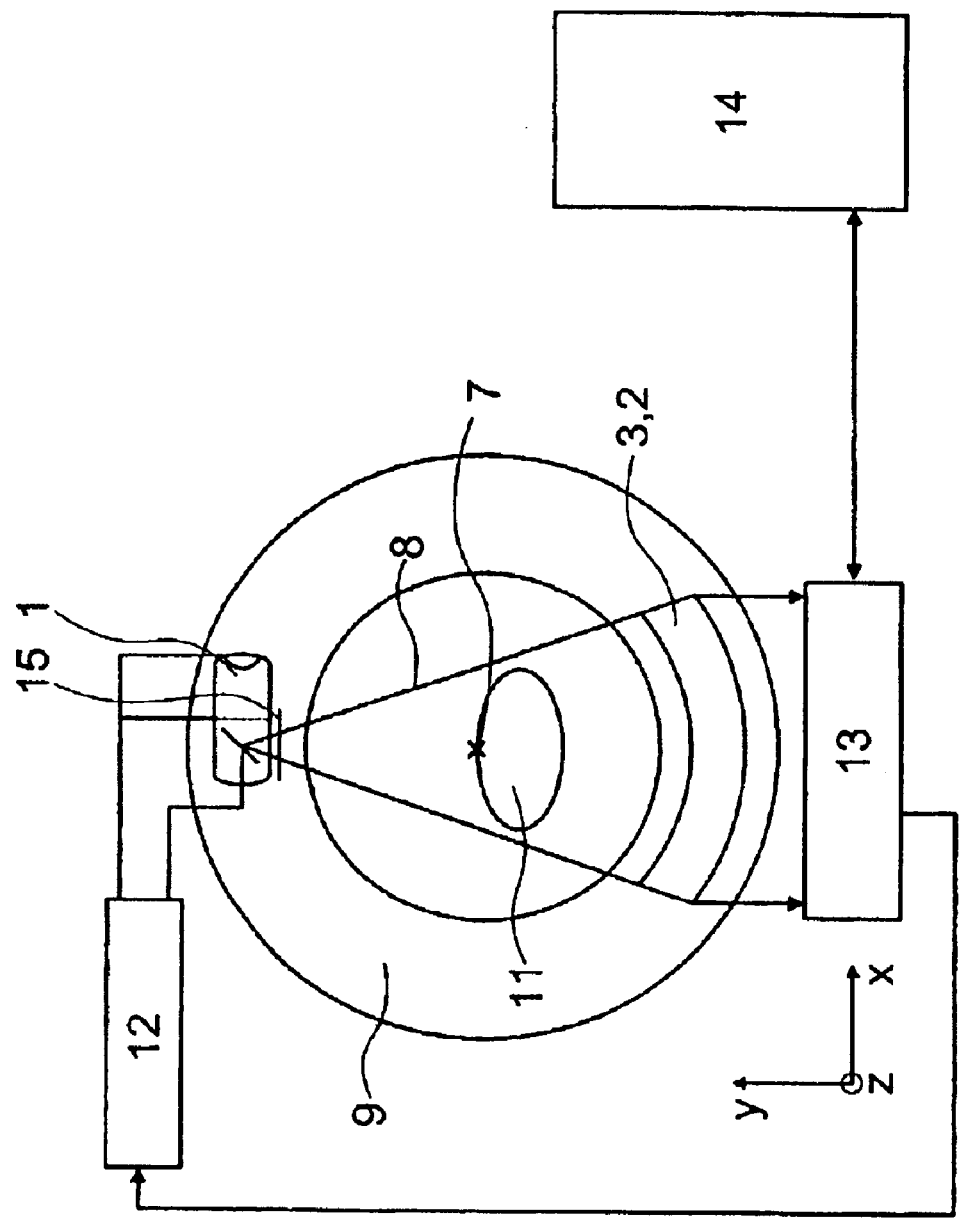
FIG. 2 shows a schematic block diagram of components of a computed tomograph for carrying out the method of an embodiment of the application.

FIG. 2 shows a different view of the computed tomograph from FIG. 1. FIG. 2 represents a schematic block diagram which shows significant system components of the present computed tomograph. In the figure, it is possible to see the gantry 9 that rotates about the rotational centre 7 during a measurement and has the X-ray tube 1 and the opposite detector row 2. The X-ray tube 1 is supplied with a high voltage of, for example, 120 kV by a high voltage generator. A controller 13 is used to drive the individual components of the computed tomograph, in particular the high voltage generator 12, the gantry 9, the detectors 3 and the patient couch, not illustrated, in order to carry out the image recording. The measured data recorded is passed on to an image computer 14, in which the image reconstruction from the measured data is carried out.

Also to be seen in the figure is the X-ray beam 8, which is widened like a fan in the layer plane and which—possibly after being attenuated by the body of the patient 10—strikes the detector elements 3. The fan-like widening of this X-ray beam 8 is defined by the aperture stop 15 arranged on the tube side.

During the operation of such a computed tomograph, extrafocal radiation from the X-ray tube, which is produced on the anode plate of the X-ray tube 1 in the vicinity of the focus, is also detected by the detector elements 3. Its spatial extent, which can be detected by the detector row 2, is determined by the one or more aperture stops 15 on the tube side. As a result, a channel-dependent distribution of the extrafocal radiation is produced. For example, in a known computed tomograph, the extrafocal radiation has an extent of about 22 mm in the centre of the detector row. It represents a projection of the anode window through the rotational centre onto the detector row. About 33 channels of the detector row of this computed tomograph correspond to this extent. This length is also needed by the convolution core used in the present method for the central detector channel. Outside the rotational centre, that is to say for the remainder of the detector channels, the anode window becomes asymmetrical and is projected with a different length onto the detector row.

Figure 3:
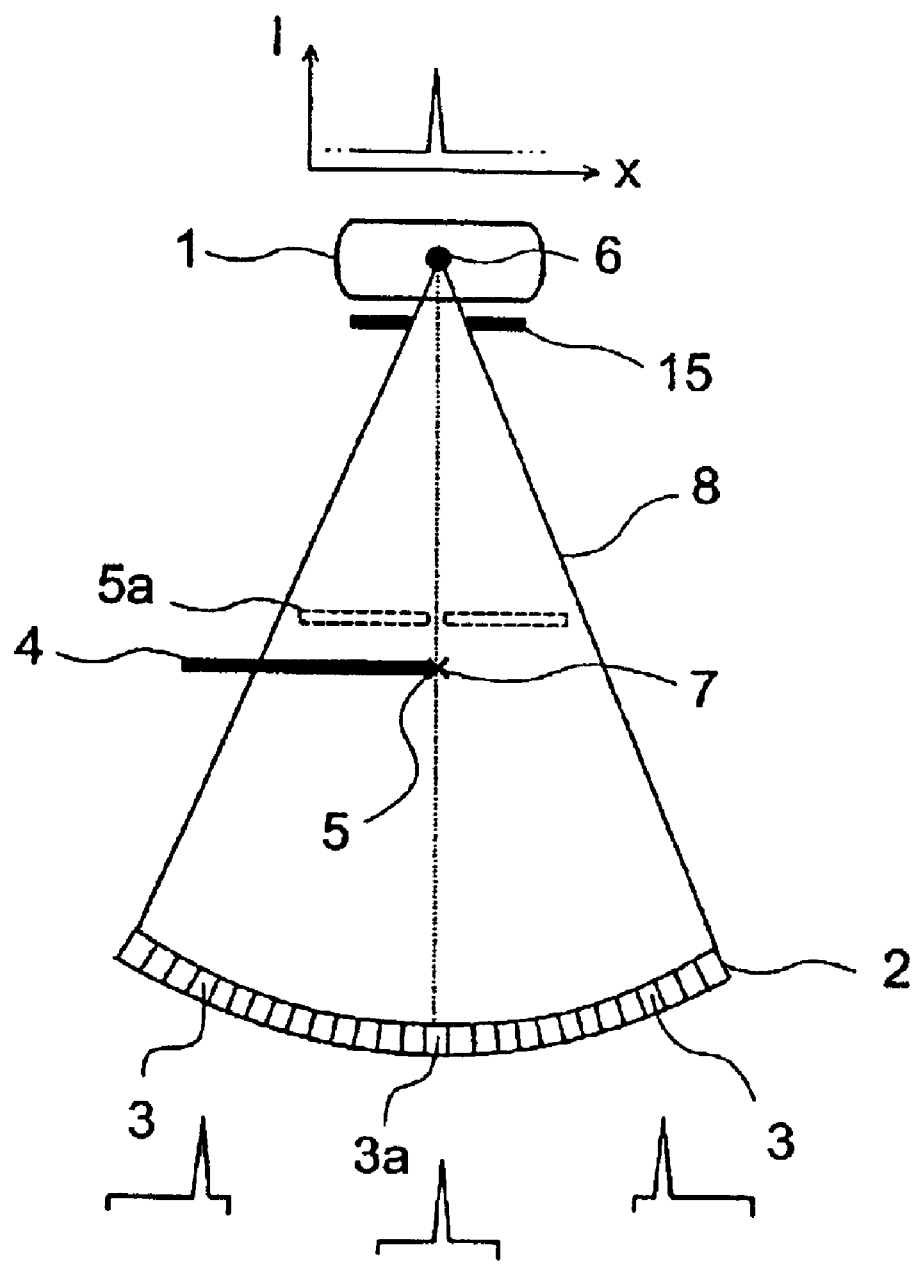
FIG. 3 shows a simplified illustration of the arrangement when determining the impulse response of the computed tomograph.

FIG. 3 shows the geometric situation in a computed tomograph, again schematically. In this figure, it is possible to see the focus 6 of the X-ray tube and the fan-like X-ray beam 8 emerging from the focus and limited by the aperture stop 15 on the tube side. The fan-like X-ray beam 8 strikes the detector row 2 having a large number of detector channels 3. In the upper part of the figure, the intensity distribution of the X-ray beams on the anode plate is illustrated schematically. In this distribution, it is possible to see the maximum of the X-rays produced by the focus, which maximum is situated on a plateau caused by extrafocal radiation. This intensity distribution is projected via the aperture stop 15 in different ways onto the individual regions of the detector row 2, as indicated in the lower part of the drawing. The image of the anode window formed by the aperture stop 15 in this case corresponds to point mirroring.

To determine the detector-channel-dependent convolution cores, in the present example an element 4 that absorbs X-rays, in the form of a lead plate with a lead edge 5, is introduced into the beam path of the X-rays, so that the lead edge 5 lies at the rotational centre 7 and over the centre of the detector row 2. Using this arrangement, a measurement is carried out which supplies a step response for the extrafocal radiation. From the measured signal profile over the individual detector channels 3, by means of simple difference formation from the signals or measured data from adjacent detector channels in each case, the impulse response can be determined. The impulse response is calculated in this case as $IM(k)=SP(k)-SP(k-1)$, $SP(k)$ representing the measured signal on the respective detector channel k, and k=2. NDET (NDET=number of detector channels). This impulse response is then Fourier transformed, the Fourier transform $H(w)$ corresponding to the impulse response $IM(k)$ of the transfer function of the system, in the present case the distribution of the extrafocal radiation.

The ideal convolution function $E(w)$ in the Fourier domain has the effect that $H(w) \times E(w)=1$. The convolution function chosen is therefore $E(w)=1/H(w)$. This convolution function $E(w)$ in the Fourier domain is then transformed back and then supplies the desired convolution core $EN(k)$ for the detector element 3a considered here which, in this example, corresponds to the central detector element of the detector row 2. The convolution core $EN(k)$ obtained here is symmetrical because of the configuration chosen in FIG. 3. The channel dependence of the distribution of the extrafocal radiation leads to unsymmetrical convolution cores, whose length additionally varies, for the other detector channels 3. The appropriate impulse response for the remaining channels can be determined from this from geometrical considerations.

A specific convolution core is therefore available for each individual detector channel 3. Since the distribution of the extrafocal radiation between adjacent detector channels is distinguished only insignificantly, it is also possible to divide up the detector row into a number of regions with a different distribution of the extrafocal radiation and in each case to use the same convolution core for all the detector channels in a region. FIG. 3 further shows, in a dashed illustration, an optical slit aperture stop Sa, which could be used in the place of the element 4 with the lead edge 5 for the direct measurement of the impulse response of the extrafocal radiation.

Figure 4:
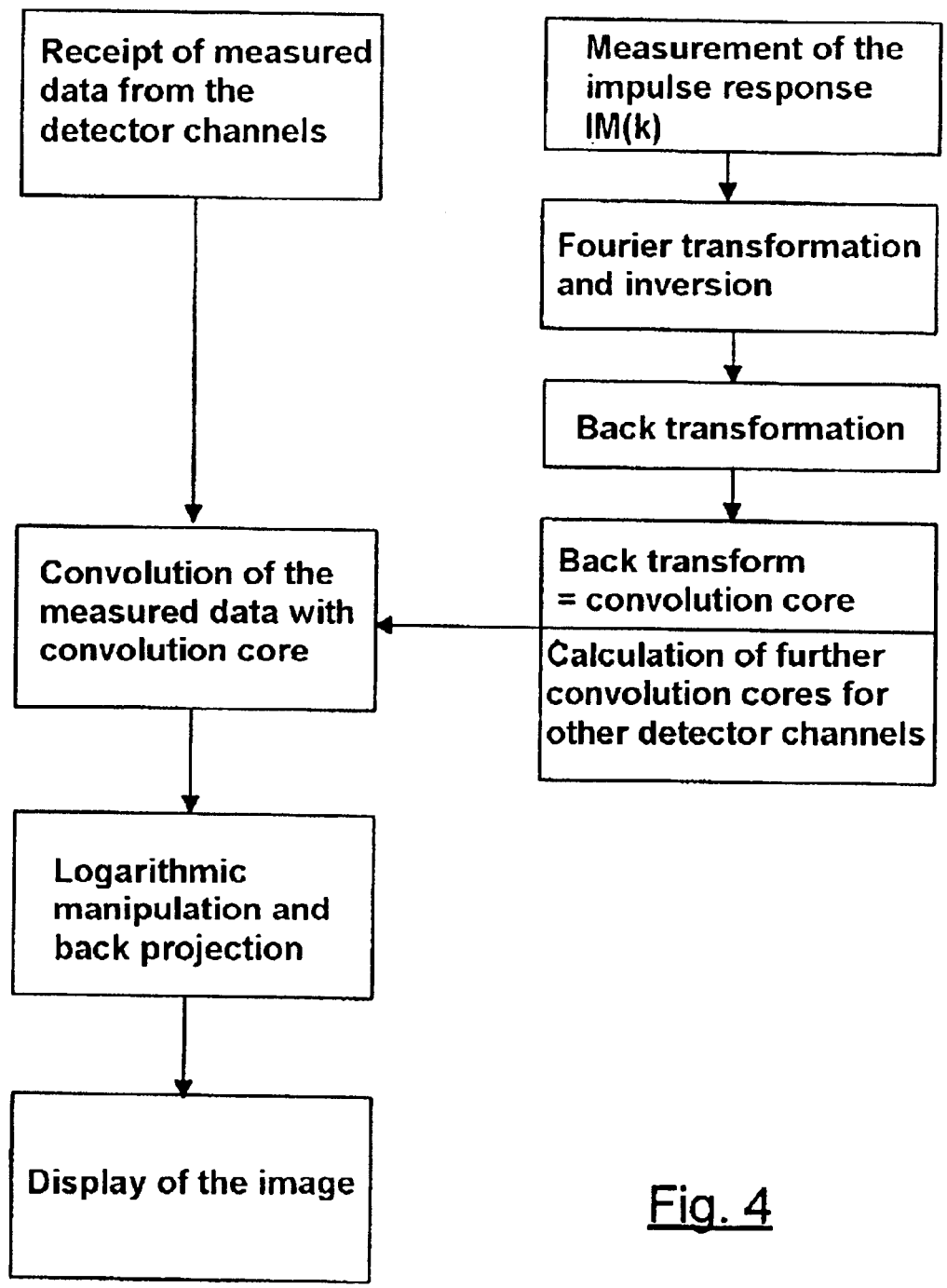
FIG. 4 shows an exemplary flowchart for carrying out the method of an embodiment of the application.

The channel-dependent convolution core is determined separately for each device type of a computed tomograph with the respectively associated tube type, and can then be used for all devices and tubes of this type to correct the extrafocal radiation. During the correction, the measured data obtained from the detector channels, before logarithmic manipulation and possible filtered back projection, is subjected to the convolution with the channel-dependent convolution core, as can be seen from the flowchart of FIG. 4. Following this convolution, corrected raw data is available, which is manipulated logarithmically in a known way and projected back with appropriate convolution cores, in order to be able to display the desired image recordings on the monitor.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of correcting extrafocal radiation of an X-ray tube in image recordings with a computed tomograph, comprising:

subjecting measured data, obtained from detector channels of at least one detector row in the computed tomography, to logarithmic manipulation and back projection in order to obtain the image recordings; and subjecting the measured data, before the logarithmic manipulation and back projection, to convolution with a detector-channel-dependent convolution core, derived from a distribution of the extrafocal radiation on at least a first detector channel of at least one of the computed tomograph and a computed tomograph of an identical type.

2. The method as claimed in claim 1, wherein, to derive the convolution core for the first detector channel, an impulse response of the extrafocal radiation of the computed tomograph is determined, a Fourier transform of the pulse response is formed and the Fourier transform is inverted and transformed back in order to obtain the convolution core for the first detector channel.

3. The method as claimed in claim 2, wherein the impulse response is obtained from a measurement of a step response of the extrafocal radiation of the computed tomograph in which an element of material that absorbs X-rays and has an edge is positioned at a distance from the detector row with the edge on a connecting line between a focus of the X-ray tube and the first detector channel, in order during the measurement to cover a number of detector channels adjoining the first detector channel.

4. The method as claimed in claim 2, wherein the impulse response is obtained directly from a measurement in which a slit aperture stop, which is narrow as compared with a focus of the X-ray tube and includes material that absorbs X-rays is positioned at a distance from the detector row on a connecting line between the focus of the X-ray tube and the first detector channel, in order during the measurement to cover a number of detector channels adjoining the first detector channel.

5. The method as claimed in claim 3, wherein at least one of the edge and the slit aperture stop is positioned at a rotational centre of the computed tomograph.

6. The method as claimed in claim 2, wherein the convolution core for detector channels other than the first detector channel is calculated from the impulse response of the computed tomograph on the first detector channel and geometric data from the computed tomograph.

7. The method as claimed in claim 1, wherein the same convolution core is used for a number of detector channels, following one another in the detector row.

8. The method as claimed in claim 4, wherein at least one of the edge and the slit aperture stop is positioned at a rotational centre of the computed tomograph.

9. The method as claimed in claim 3, wherein the convolution core for detector channels other than the first detector channel is calculated from the impulse response of the computed tomograph on the first detector channel and geometric data from the computed tomograph.

10. The method as claimed in claim 4, wherein the convolution core for detector channels other than the first detector channel is calculated from the impulse response of the computed tomograph on the first detector channel and geometric data from the computed tomograph.

11. The method as claimed in claim 5, wherein the convolution core for detector channels other than the first detector channel is calculated from the impulse response of the computed tomograph on the first detector channel and geometric data from the computed tomograph.

12. The method as claimed in claim 8 wherein the convolution core for detector channels other than the first detector channel is calculated from the impulse response of the computed tomograph on the first detector channel and geometric data from the computed tomograph.

13. A method of correcting extrafocal radiation of an X-ray tube in an image recording with a computed tomograph, comprising:

subjecting measured data to convolution with a detector-channel-dependent convolution core, derived from a distribution of the extrafocal radiation on at least a first detector channel of at least one of the computed tomograph and a computed tomograph of an identical type; and subjecting the measured data obtained from detector channels of at least one detector row in the computed tomography, to logarithmic manipulation and back projection in order to obtain the image recording.

14. The method as claimed in claim 13, wherein, to derive the convolution core for the first detector channel, an impulse response of the extrafocal radiation of the computed tomograph is determined, a Fourier transform of the pulse response is formed and the Fourier transform is inverted and transformed back in order to obtain the convolution core for the first detector channel.

15. The method as claimed in claim 14, wherein the impulse response is obtained from a measurement of a step response of the extrafocal radiation of the computed tomograph in which an element of material that absorbs X-rays and has an edge is positioned at a distance from the detector row with the edge on a connecting line between a focus of the X-ray tube and the first detector channel, in order during the measurement to cover a number of detector channels adjoining the first detector channel.

16. The method as claimed in claim 14, wherein the impulse response is obtained directly from a measurement in which a slit aperture stop, which is narrow as compared with a focus of the X-ray tube and includes material that absorbs X-rays is positioned at a distance from the detector row on a connecting line between the focus of the X-ray tube and the first detector channel, in order during the measurement to cover a number of detector channels adjoining the first detector channel.

17. The method as claimed in claim 15, wherein at least one of the edge and the slit aperture stop is positioned at a rotational centre of the computed tomograph.

18. The method as claimed in claim 14, wherein the convolution core for detector channels other than the first detector channel is calculated from the impulse response of the computed tomograph on the first detector channel and geometric data from the computed tomograph.

19. The method as claimed in claim 13, wherein the same convolution core is used for a number of detector channels, following one another in the detector row.

20. The method as claimed in claim 16, wherein at least one of the edge and the slit aperture stop is positioned at a rotational centre of the computed tomograph.

* * * * *